(12) United States Patent
Hou

(10) Patent No.: US 10,184,857 B2
(45) Date of Patent: Jan. 22, 2019

(54) IMPACT TEST DEVICE AND METHOD

(71) Applicant: The Yokohama Rubber Co., LTD., Minato-ku, Tokyo (JP)

(72) Inventor: Gang Hou, Hiratsuka (JP)

(73) Assignee: The Yokohama Rubber Co., LTD. (JP)

( * ) Notice: Subject to any disclaimer, the term of this patent is extended or adjusted under 35 U.S.C. 154(b) by 119 days.

(21) Appl. No.: 15/512,048

(22) PCT Filed: Aug. 26, 2015

(86) PCT No.: PCT/JP2015/074070
§ 371 (c)(1),
(2) Date: Jun. 26, 2017

(87) PCT Pub. No.: WO2016/042999
PCT Pub. Date: Mar. 24, 2016

(65) Prior Publication Data
US 2017/0292895 A1    Oct. 12, 2017

(30) Foreign Application Priority Data
Sep. 16, 2014    (JP) .................................. 2014-187961

(51) Int. Cl.
*B65G 15/32*    (2006.01)
*G01N 3/40*    (2006.01)
(Continued)

(52) U.S. Cl.
CPC ............... *G01M 7/08* (2013.01); *B65G 15/32* (2013.01); *G01K 13/08* (2013.01); *G01N 3/34* (2013.01);
(Continued)

(58) Field of Classification Search
None
See application file for complete search history.

(56) References Cited

U.S. PATENT DOCUMENTS 3,964,348 A * 6/1976 Dawson ................. B23D 63/18
76/26
4,313,337 A * 2/1982 Myint ..................... G01N 3/34
73/12.13

(Continued)

FOREIGN PATENT DOCUMENTS

| JP | 2001-506740 | 5/2001 |
| JP | 2008-233016 | 10/2008 |

(Continued)

OTHER PUBLICATIONS

International Search Report for International Application No. PCT/JP2015/074070 dated Nov. 17, 2015, 4 pages, Japan.

*Primary Examiner* — Peter Macchiarolo
*Assistant Examiner* — Jermaine Jenkins
(74) *Attorney, Agent, or Firm* — Thrope North & Western

(57) ABSTRACT

The present technology provides an impact test device and method. The rotational speed of a rotary drum with a rubber sample attached on the outer surface is set to a desired rotational speed, the impact cycle for the surface of the rubber sample of the contact member by the repeat-impact mechanism is set to a desired cycle, the impact load by the contact member is set to a desired impact load by a weight member, a desired contact member is selected from among the plurality of contact members with different specifications, and the contact member is repeatedly made to collide with the surface of the rubber sample by rotating a vertical excitation roller and pivoting the arm portion in the vertical direction with a rotation shaft.

9 Claims, 6 Drawing Sheets

(51) Int. Cl.
　　　*G01K 13/08*　　　(2006.01)
　　　*G01M 7/08*　　　(2006.01)
　　　*G01N 3/34*　　　(2006.01)
　　　*G01L 5/00*　　　(2006.01)
　　　*G01N 3/31*　　　(2006.01)

(52) U.S. Cl.
　　　CPC ............. *G01N 3/40* (2013.01); *G01L 5/0052* (2013.01); *G01N 3/31* (2013.01)

(56) References Cited

U.S. PATENT DOCUMENTS

| | | | | |
|---|---|---|---|---|
| 4,537,060 | A * | 8/1985 | Underwood | G01N 3/31 73/12.09 |
| 6,026,681 | A | 2/2000 | Wunderer et al. | |
| 7,284,445 | B2 * | 10/2007 | Ido | G01M 7/08 73/801 |
| 2016/0377519 | A1 * | 12/2016 | Norman | G01N 3/56 73/7 |

FOREIGN PATENT DOCUMENTS

| | | |
|---|---|---|
| JP | 2011-237299 | 11/2011 |
| JP | 2012-242200 | 12/2012 |
| JP | 2014-040295 | 3/2014 |
| WO | WO 1997/19425 | 5/1997 |

\* cited by examiner

IMPACT TEST DEVICE AND METHOD

TECHNICAL FIELD

The present technology relates to an impact test device and method, and more particularly, to an impact test device and method that can accurately predict impact resistance of an upper cover rubber of a conveyor belt should the conveyor be actually used.

BACKGROUND ART

Various objects, including mineral resources such as iron ore and limestone, are conveyed by a conveyor belt. When the objects are conveyed by the conveyor belt, the objects to be conveyed are fed onto an upper cover rubber of the conveyor belt from a hopper or another conveyor belt. The fed objects to be conveyed are carried on the upper cover rubber and conveyed in a traveling direction of the conveyor belt. When the objects to be conveyed are fed onto the upper cover rubber of the conveyor belt, the upper cover rubber is subject to impact, and when the surfaces of the objects to be conveyed are sharp, the upper cover rubber sometimes sustains cut damage. Thus, in known art, various proposals have been made (see Japanese Unexamined Patent Application Publication No. 2014-40295A for example) in order to improve the cut resistance of the upper cover rubber.

A size and occurrence frequency of the cut damage, a wear amount, and the like occurring in the upper cover rubber significantly change depending on use conditions of the conveyor belt (including types of the objects to be conveyed). Because of this, it is preferable to perform an evaluation with requirements resembling the actual use conditions in order to accurately predict the impact durability of the upper cover rubber as much as possible. Because of this, it is required for a test device that performs evaluation to be able to set requirements matching various use conditions of the conveyor belt.

Though the object to be evaluated is not an upper cover rubber of a conveyor belt, an impact cushioning evaluation device with the purpose of evaluating the impact cushioning of a cushion body for a human such as an impact absorbing pad is known (see Japanese Unexamined Patent Application Publication No. 2008-233016A). The evaluation device proposed in Japanese Unexamined Patent Application Publication No. 2008-233016A is provided with a bar having an impactor disposed on a front end portion, and a back end portion pivoted by a rotation shaft. It is configured so that after the impactor is moved upward by pivoting the bar with the rotation shaft as the center, the impactor can be made to collide with the object to be evaluated disposed below by lowering the impactor downward. For conveyor belts, the objects to be conveyed continuously collides with the upper cover rubber. Furthermore, the objects to be conveyed collide with an upper cover rubber that is moving. Because of these reasons, it is not possible to reproduce requirements resembling actual use conditions of a conveyor belt.

SUMMARY

The present technology provides an impact test device and a method whereby the impact resistance of an upper cover rubber of a conveyor belt should the conveyor belt be actually use can be accurately predicted.

An impact test device of the present technology is provided with a rotary drum with variable rotational speed, a contact member able to be brought into contact with a surface of a rubber sample attached on an outer surface of the rotary drum, a repeat-impact mechanism that repeatedly makes the contact member collide with the surface of the rubber sample, and a weight member that changes the impact load imparted by the contact member, an impact cycle for the surface of the rubber sample of the contact member by the repeat-impact mechanism being changeable, the contact member including a plurality of contact members with varying specifications for a contact surface that comes into contact with the surface of the rubber sample, and a discretionary contact member that collides with the surface of the rubber sample being selected from among the plurality of contact members.

An impact test method of the present technology for a rubber sample attached on an outer surface of a rotary drum with variable rotational speed in which a contact member is made to repeatedly collide with a surface of the rubber sample by a repeat-impact mechanism, the method comprising the steps of: setting a rotational speed of the rotary drum to a desired speed, setting an impact cycle for the surface of the rubber sample of the contact member by the repeat-impact mechanism to a desired cycle, setting an impact load imparted by the contact member to a desired impact load by a weight member, and selected as the contact member a desired contact member from among a plurality of contact members with varying specifications for a contact surface that comes into contact with the surface of the rubber surface, and repeatedly colliding the desired contact member with the surface of the rubber sample.

According to the present technology, the rotational speed of the rotary drum, the impact cycle for the surface of the rubber sample of the contact member, and the impact load from the contact member can be set as desired. The contact member having the contact surface of desired specifications can be repeatedly caused to collide with the surface of the rubber sample. By this, it is possible to perform evaluation with requirements resembling actual use conditions of a conveyor belt when testing the impact resistance of a rubber sample with the same specifications as rubber used for an upper cover rubber of the conveyor belt. Therefore, the impact resistance of an upper cover rubber of a conveyor belt should the conveyor belt be actually used can be accurately predicted.

Here, a casing can be provided on the impact testing device of the present technology that makes it possible to change an external environment temperature of the rubber sample. By this, because the external environment temperature of the rubber sample can be set to a desired temperature, it becomes possible to perform evaluation with requirements more resembling actual use conditions of a conveyor belt.

Furthermore, it is possible to provide a temperature sensor that detects the surface temperature of the rubber sample. By this, it is possible to measure the change in surface temperature of the rubber sample being evaluated, and understand the energy generated by the rubber sample when worn or damaged.

The repeat-impact mechanism is provided with, for example, an arm portion with the contact member attached to one end portion thereof in the longitudinal direction, and a vertical excitation unit for exciting another end portion in the longitudinal direction of the arm portion in the vertical direction, and has a configuration wherein the position partway along the longitudinal direction of the arm portion is supported by the rotation shaft such that the arm portion can pivot in the vertical direction about the rotation shaft. Alternatively, the repeat-impact mechanism is provided with a rotating roller with the contact member attached on the outer surface thereof, and has a configuration wherein the rotating roller is supported so that it can move in the vertical direction, and is rotated by the rotational force of the rotary drum upon the contact member making contact with the surface of the rubber sample.

DETAILED DESCRIPTION

Figure 1:
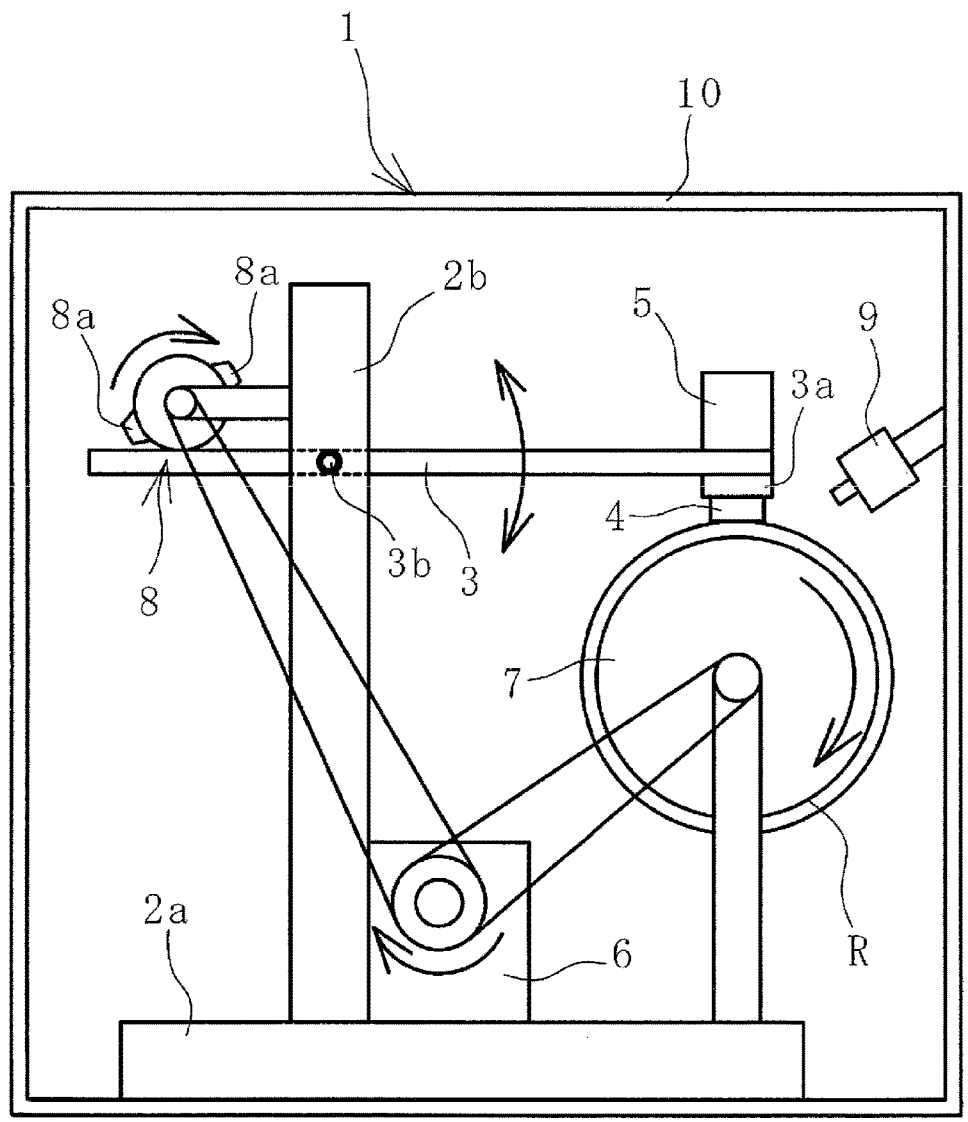
FIG. 1 is an explanatory diagram illustrating, in a front view, an impact test device of the present technology.
Figure 1:
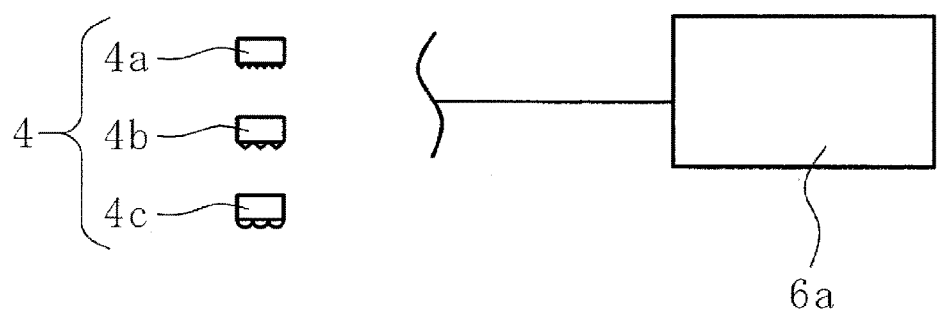

An impact test device and method of the present technology will be described below with reference to an embodiment illustrated in the drawings.

Figure 6:
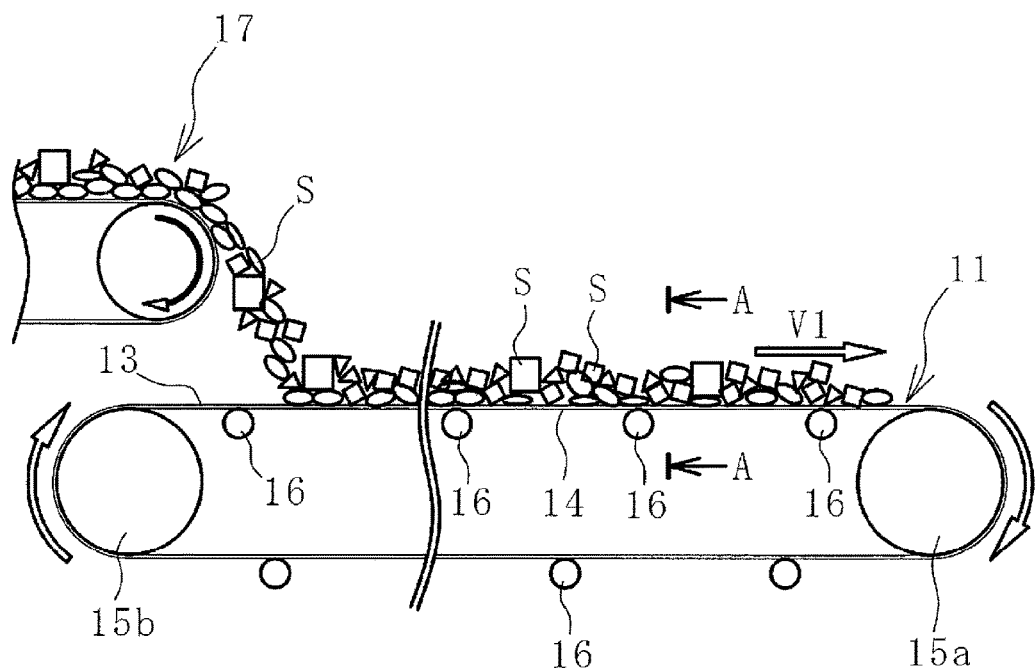
FIG. 6 is an explanatory view illustrating a conveyor belt line in a simplified manner.
Figure 7:
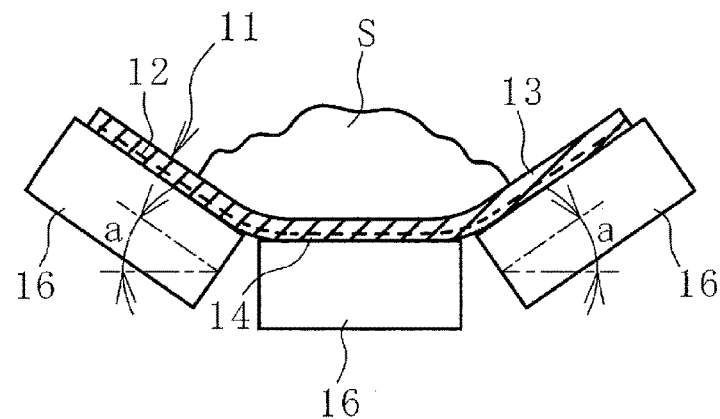
FIG. 7 is a cross-sectional view taken along A-A of FIG. 6.

In an actual conveyor belt line, as illustrated in FIGS. 6 and 7, objects to be conveyed S conveyed by another conveyor belt 17 are fed onto a conveyor belt 11 and conveyed to a conveying destination by this conveyor belt 11. The objects to be conveyed S may be fed onto the conveyor belt 11 by a hopper and the like. The conveyor belt 11 is stretched at a prescribed tension between pulleys 15a and 15b.

The conveyor belt 11 is constituted by a core layer 12 constituted by a core made of canvas, steel cords, or the like, and an upper cover rubber 13 and a lower cover rubber 14 that sandwich the core layer 12. The core layer 12 is a member bearing the tension that causes the conveyor belt 11 to be stretched. The lower cover rubber 14 is supported by a support roller 16 on a carrier side of the conveyor belt 11, and the upper cover rubber 13 is supported by the support roller 16 on a return side of the conveyor belt 11. Three of the support rollers 16 are arranged on the carrier side of the conveyor belt 11 in the belt width direction. The conveyor belt 11 is supported by these support rollers 16 in a concave shape having a prescribed trough angle a. When the pulley 15a on a drive side is rotationally driven, the conveyor belt 11 is operated in one direction at a prescribed traveling speed V1. The objects to be conveyed S are fed onto the upper cover rubber 13, and are loaded on the upper cover rubber 13 and conveyed.

Figure 2:
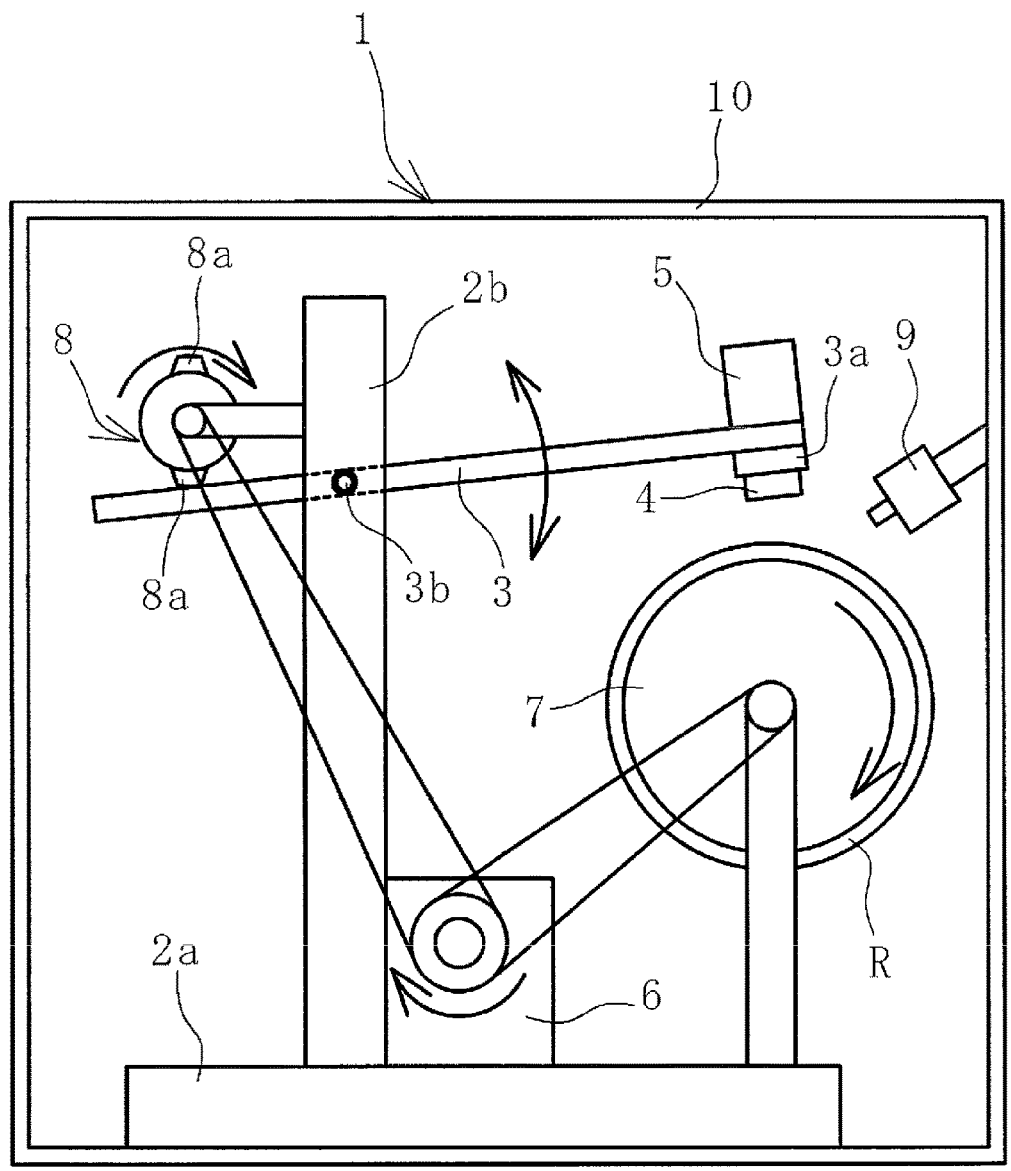
FIG. 2 is an explanatory diagram illustrating a state where a contact member in FIG. 1 has moved to an upper position.
Figure 3:
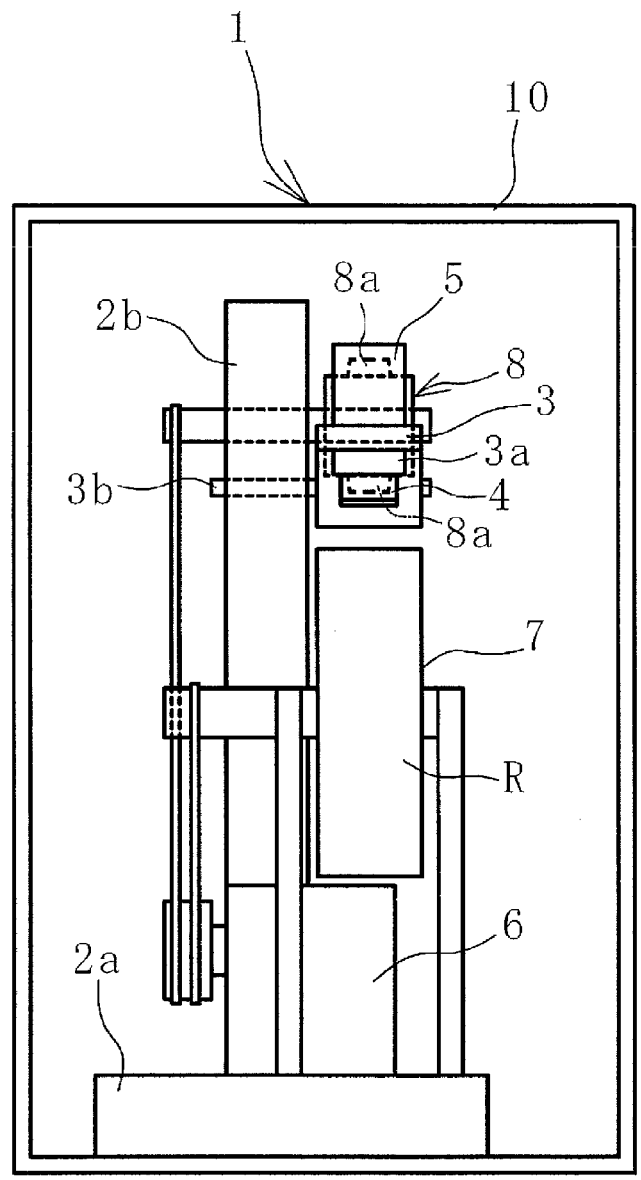
FIG. 3 is an explanatory diagram illustrating, in a side view, the impact test device in FIG. 2.

The impact test device 1 of the present technology illustrated in FIGS. 1 to 3 is provided with a rotary drum 7, a contact member 4, an arm portion 3 with the contact member 4 removably attached, a weight member 5 removably attached to the arm portion 3, and a control unit 6a. Furthermore, a temperature sensor 9, and a casing 10 with the components described above excluding the control unit 6a installed therein, are provided in this embodiment.

The casing 10 can set and maintain an internal space at a desired temperature. In addition to temperature, it is also possible to apply a casing 10 that can set and maintain an internal space at a desired humidity.

The rotary drum 7 is rotatably supported on a support platform installed on a base 2a. The rotary drum 7 is rotationally driven by a drive motor 6 via a transmission belt. The rotational speed of the rotary drum, 7 is variable, and a desired rotational speed can be set. This rotational speed is controlled by the control unit 6a.

A rubber sample R is attached on the outer surface of the rotary drum 7. In this embodiment, the rubber sample R is attached around the entire outer surface of the rotary drum 7 to form an annular shape. The temperature sensor 9 detects the surface temperature of the rubber sample R.

The arm portion 3 is fixed to a post 2b that is fixed to the base 2a in an upright position by being supported by a rotation shaft 3b allowing for pivoting in the vertical direction. The contact member 4 and the weight member 5 are attached to one end portion in the longitudinal direction of the arm portion 3. A vertical excitation roller 8 fixed to the post 2b is installed on the other end portion in the longitudinal direction of the arm portion 3. The vertical excitation roller 8 is rotationally driven by the drive motor 6 via the transmission belt.

The rotating roller 7, the vertical excitation roller 8, and the drive roller 6 can have a configuration wherein driving force is transmitted by another mechanism such as a gear. Furthermore, the rotating roller 7 and the vertical excitation roller 8 can have a configuration rotationally driven by a separate drive source.

The vertical excitation roller 8 rotates while the outer surface is in contact with the upper surface of the arm portion 3. Protrusions 8a protrude at intervals in the peripheral direction on the outer surface of the vertical excitation roller 8. As described later, this arm portion 3 and vertical excitation roller 8 configure the repeat-impact mechanism that repeatedly causes the contact member 4 to collide with the surface of the rubber sample R.

By making the protrusions 8a removable, the peripheral direction intervals and protrusion height of the protrusions 8a on the vertical excitation roller 8 can be made different. Furthermore, a plurality of vertical excitation rollers 8 can be provided with different peripheral direction intervals and protrusion heights of the protrusions 8a.

The contact member 4 is attached to one end portion in the longitudinal direction of the arm portion 3 so that it can make contact with the surface of the rubber sample R. More specifically, the contact member 4 is removably attached to a holding portion 3a fixed on one end portion in the longitudinal direction of the arm portion 3.

A plurality of contact members are provided as the contact member 4, with varying specifications (shape, hardness, material, surface roughness, and the like) for the contact surface that contacts the surface of the rubber surface R. In other words, the contact members 4 (4a, 4b, and 4c) are provided having a contact surface with specifications resembling the surface of the objects to conveyed S conveyed by the conveyor belt 11, in which rubber with the same specifications as the rubber sample R is used as the upper cover rubber 13.

For example, because the sharpness, hardness, and the like differ depending on whether the objects to be conveyed S are iron ore, limestone, or gravel, a plurality of contact members 4 may be provided having contact surfaces resembling these. A discretionary contact member 4 may then be selected from among the plurality of contact members 4, and attached to the holding portion 3a.

The other end portion in the longitudinal direction of the arm portion 3 is excited in the vertical direction by the vertical excitation roller 8 rotating. Along with this, the arm portion 3 pivots in the vertical direction with the rotation shaft 3b as the center, the rotation shaft 3b being in a position partway along the longitudinal direction of the arm portion 3. Because of this, the one end portion in the longitudinal direction of the arm portion 3 is excited in the vertical direction in the opposite direction of the other end portion. The contact member 4 is also excited in the vertical direction, the state illustrated in FIG. 1 and the state illustrated in FIG. 2 are repeated, and the contact member 4 repeatedly collides with the surface of the rubber sample R. In the present embodiment, the contact member 4 collides with the surface of the rubber sample R at a position directly above the rotary drum 7 (rotational center shaft).

A plurality of weight members 5 with different weights are provided as the weight member 5, and are removably attached on the one end portion in the longitudinal direction of the arm portion 3. The weight member 5 may change the impact load the contact member 4 imparts on the rubber sample R. In other words, the impact force on the surface of the rubber sample R of the contact member 4 can be changed depending on the weight member 5.

This test device 1 has a changeable structure wherein the impact cycle for the surface of the rubber sample R of the contact member 4 changes when the rotational speed of the vertical excitation roller 8 is changed. Furthermore, the impact cycle described above also changes depending on the pitch in the peripheral direction at which the protrusions 8a are arranged.

Because the amplitude in the vertical direction of the contact member 4 changes when the protrusion height of the protrusions 8a are changed, the impact force on the surface of the rubber sample R of the contact member 4 can be changed. The position in the longitudinal direction of the arm portion 3 of the rotation shaft 3b may also be changed. Furthermore, the position in the longitudinal direction that comes into contact with the arm portion 3 of the vertical excitation roller 8 can be changed. Because the amplitude in the vertical direction of the contact member 4 changes with these configurations, the impact force on the surface of the rubber sample R of the contact member 4 can be changed.

Next, the test method for evaluating the impact resistance of the rubber sample R using the impact test device 1 is described.

The rubber sample R that becomes the object to be evaluated is attached on the outer surface of the rotary drum 7, and the drive motor 6 is rotationally driven. At this time, the rotational speed of the rotary drum 7 is set to a desired speed, the impact cycle for the surface of the rubber sample R of the contact member 4 by the repeat-impact mechanism is set to a desired cycle, and the impact load imparted by the contact member 4 is set to a desired impact load by the weight member 5.

A desired contact member from the plurality of contact members 4 (4a, 4b, and 4c) is selected as the contact member 4 and is mounted to the holding portion 3a. Then, a desired contact member 4 is repeatedly made to collide with the surface of the rubber sample R.

According to the present technology, it becomes possible to perform evaluation with conditions resembling actual use conditions of the conveyor 11 wherein rubber with the same specifications as the rubber sample R that becomes the object to be evaluated is used as the upper cover rubber 13. In other words, the rotational speed of the rotary drum 7 is made to have similar conditions to the traveling speed of the conveyor belt 11. The impact cycle of the contact member 4 is made to have similar requirements to the feeding frequency of the object to be conveyed S to the conveyor belt 11. The impact load imparted by the contact member 4 is made to have similar requirements to the impact load that the upper cover rubber 13 receives from the object to be conveyed S, based on the feeding height, specific weight, and the like of the object to be conveyed S.

By these, requirements can be made resembling actual use conditions of the conveyor belt 11. Therefore, the impact resistance (damage condition, worn amount and the like) of the upper cover rubber 13 of the conveyor belt 11 during actual use can be accurately predicted.

In the present embodiment, the external environment temperature of the rubber sample R can be set at a desired temperature by the casing 10. Because of this, it becomes possible to perform evaluation with conditions more resembling actual use conditions of the conveyor belt 11. Furthermore, by performing evaluation by changing the external environment temperature, the temperature dependency of the impact resistance of the rubber sample R can be understood.

Furthermore, the change in surface temperature of the rubber sample R being evaluated can be measured because the temperature sensor 9 is provided. Because heat energy is generated when the rubber sample R is worn or damaged, it is possible to understand the energy during wearing or damage by the temperature measurement result of the temperature sensor 9. Because the size of this energy is different depending on the type of rubber, the temperature measurement result is effective for selecting a type of rubber that can make this energy smaller.

Figure 4:
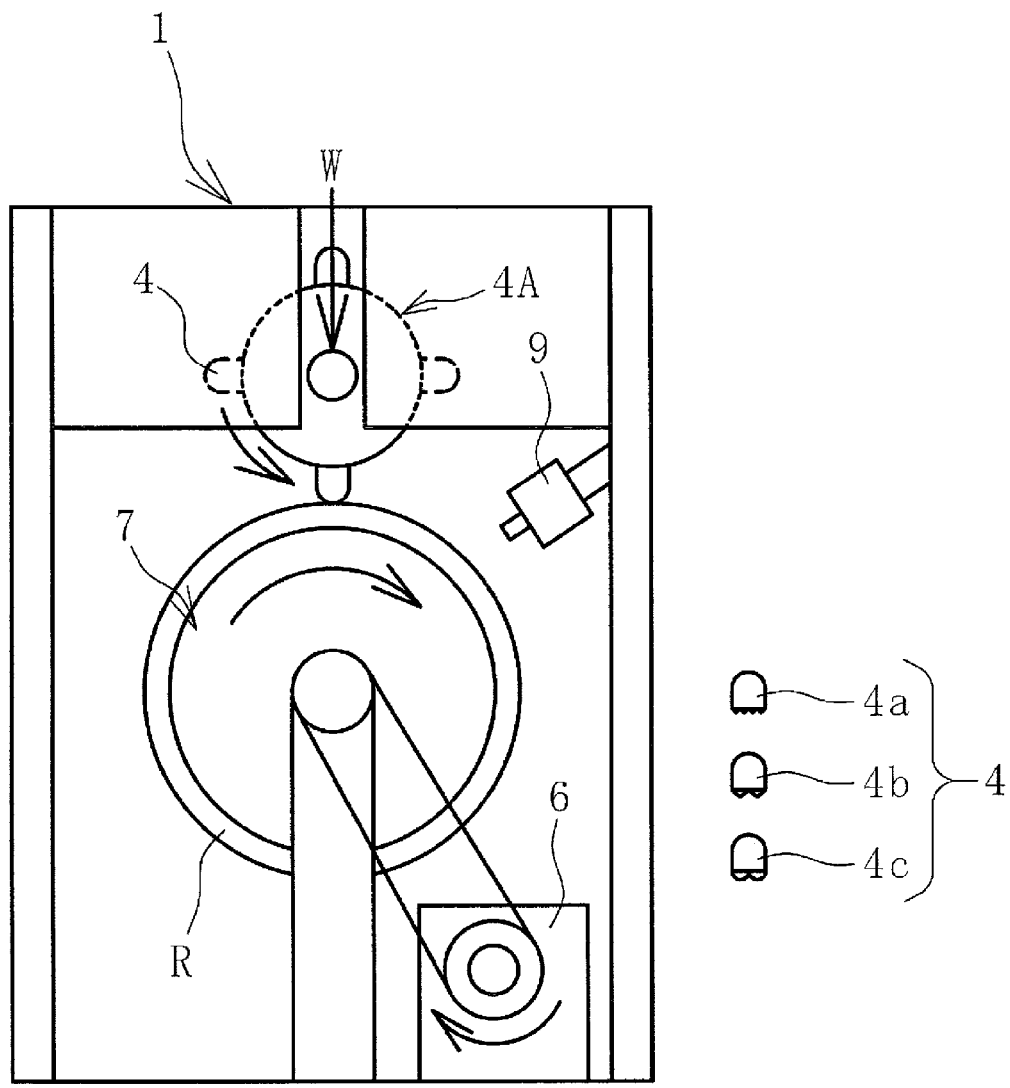
FIG. 4 is an explanatory diagram illustrating, in a front view, an impact test device of another embodiment.
Figure 5:
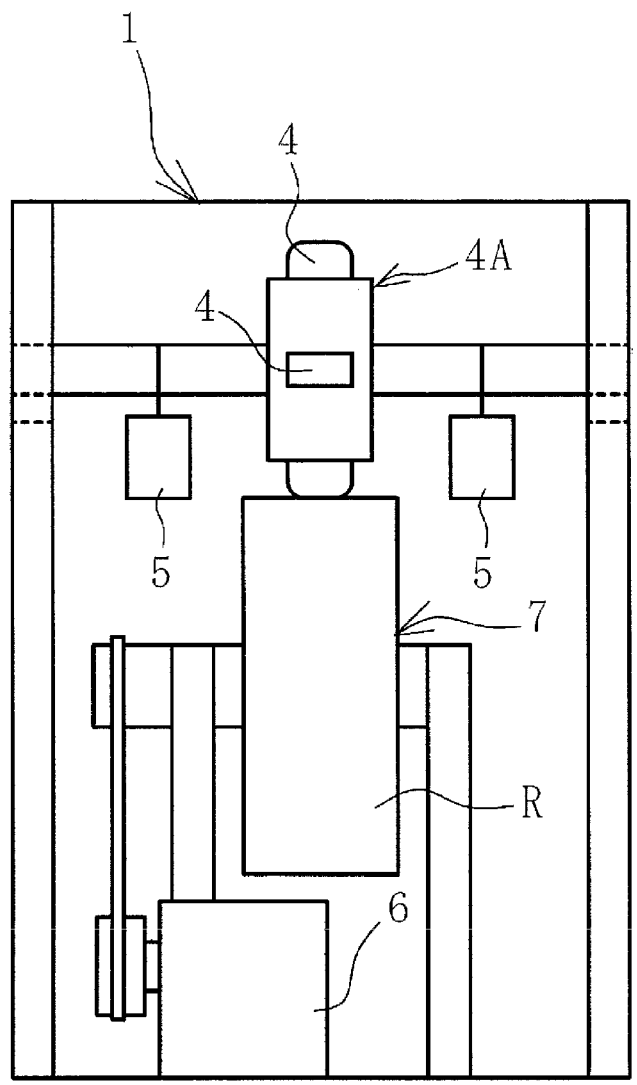
FIG. 5 is an explanatory drawing illustrating, in a side view, the impact test device in FIG. 4.

The repeat-impact mechanism is not limited to the embodiment described above, and can be a mechanism such as that provided with the embodiment illustrated in FIGS. 4 and 5. The repeat-impact mechanism in this embodiment is provided with a rotating roller 4A with the contact member 4 attached on the outer surface. This rotating roller 4A is supported so that it can move in the vertical direction.

The rotating roller 4A rotates by the rotational force of the rotary drum 7, by the contact member 4 contacting the rubber sample R attached on the outer surface of the rotary drum 7. In other words, the rotating roller 4A automatically rotates by the rotary drum 7 rotating. By this, the contact member 4 is made to repeatedly collide with the surface of the rubber sample R.

In the present embodiment, the rotating roller 4A functions as the repeat-impact mechanism. Furthermore, the weight member 5 is provided as illustrated in FIG. 5, but the rotating roller 4A can be made to function as the weight member 5. In other words, the weight of the rotating roller 4A is adjusted to set to a desired impact load. Alternatively, a rotating roller 4A with the appropriate weight is used.

The invention claimed is:

1. An impact test device, comprising:
a rotary drum with variable rotational speed;
a contact member able to be brought into contact with a surface of a rubber sample attached on an outer surface of the rotary drum;
a repeat-impact mechanism that repeatedly makes the contact member collide with the surface of the rubber sample; and
a weight member that changes the impact load imparted by the contact member;
an impact cycle for the surface of the rubber sample of the contact member by the repeat-impact mechanism being changeable;

the contact member including a plurality of contact members with varying specifications for a contact surface that comes into contact with the surface of the rubber sample; and a discretionary contact member that collides with the surface of the rubber sample being selected from among the plurality of contact members.

2. The impact test device according to claim 1, comprising a casing that can change an external environment temperature of the rubber sample.

3. The impact test device according to claim 2, comprising a temperature sensor that detects a surface temperature of the rubber sample.

4. The impact test device according to claim 1, comprising a temperature sensor that detects a surface temperature of the rubber sample.

5. The impact test device according to claim 1, wherein the repeat-impact mechanism comprises an arm portion with the contact member attached to one end portion thereof in the longitudinal direction, and a vertical excitation unit for exciting another end portion in the longitudinal direction of the arm portion in a vertical direction; and a position partway along the longitudinal direction of the arm portion is supported by a rotation shaft such that the arm portion can pivot in the vertical direction about the rotation shaft.

6. The impact test device according to claim 1, wherein the repeat-impact mechanism comprises a rotating roller with the contact member attached on an outer surface thereof, the rotating roller being supported so that it can move in the vertical direction, and being rotated by rotational force of the rotary drum upon the contact member making contact with the surface of the rubber sample.

7. An impact test method for a rubber sample attached on an outer surface of a rotary drum with variable rotational speed in which a contact member is made to repeatedly collide with a surface of the rubber sample by a repeat-impact mechanism, the method comprising the steps of:

setting a rotational speed of the rotary drum to a desired speed;

setting an impact cycle for the surface of the rubber sample of the contact member by the repeat-impact mechanism to a desired cycle;

setting an impact load imparted by the contact member to a desired impact load by a weight member; and selecting as the contact member a desired contact member from among a plurality of contact members with varying specifications for a contact surface that comes into contact with the surface of the rubber surface, and repeatedly colliding the desired contact member with the surface of the rubber sample.

8. The impact test device according to claim 3, wherein the repeat-impact mechanism comprises an arm portion with the contact member attached to one end portion thereof in the longitudinal direction, and a vertical excitation unit for exciting another end portion in the longitudinal direction of the arm portion in a vertical direction; and a position partway along the longitudinal direction of the arm portion is supported by a rotation shaft such that the arm portion can pivot in the vertical direction about the rotation shaft.

9. The impact test device according to claim 8, wherein the repeat-impact mechanism comprises a rotating roller with the contact member attached on an outer surface thereof, the rotating roller being supported so that it can move in the vertical direction, and being rotated by rotational force of the rotary drum upon the contact member making contact with the surface of the rubber sample.

* * * * *